US012558002B2

(12) United States Patent
Receveur et al.

(10) Patent No.: US 12,558,002 B2
(45) Date of Patent: Feb. 24, 2026

(54) BED SCALE NOISE COMPENSATION USING A REFERENCE TRANSDUCER

(71) Applicant: Hill-Rom Services, Inc., Batesville, IN (US)

(72) Inventors: Timothy J. Receveur, Apex, NC (US); Sinan Batman, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 687 days.

(21) Appl. No.: 17/895,550

(22) Filed: Aug. 25, 2022

(65) Prior Publication Data

US 2023/0127922 A1     Apr. 27, 2023

Related U.S. Application Data

(60) Provisional application No. 63/238,937, filed on Aug. 31, 2021.

(51) Int. Cl.

| | |
|---|---|
| *A61B 5/11* | (2006.01) |
| *A61B 5/00* | (2006.01) |
| *A61G 7/05* | (2006.01) |
| *G16H 10/60* | (2018.01) |
| *G16H 40/67* | (2018.01) |

(52) U.S. Cl.
CPC ............ *A61B 5/1113* (2013.01); *A61B 5/002* (2013.01); *A61B 5/6892* (2013.01); *A61B 5/704* (2013.01); *A61B 5/721* (2013.01); *A61B 5/725* (2013.01); *A61G 7/0527* (2016.11); *G16H 10/60* (2018.01); *G16H 40/67* (2018.01); *A61B 2562/0219* (2013.01); *A61B 2562/0252* (2013.01); *A61B 2562/046* (2013.01); *A61G 2203/30* (2013.01)

(58) Field of Classification Search
CPC ....... A61B 5/002; A61B 5/6892; A61B 5/704; A61B 5/721; A61B 2562/0219; A61B 2562/0252; A61B 2562/046; A61B 5/7264; A61B 5/1118; A61B 5/7203; A61B 5/6891; A61G 7/0527; A61G 7/015; A61G 7/05; A61G 2203/32; A61G 2203/44; A61G 7/018; G16H 10/60; G16H 40/20; G16H 40/63
See application file for complete search history.

(56) References Cited

U.S. PATENT DOCUMENTS

| | | | | |
|---|---|---|---|---|
| 6,353,950 | B1 * | 3/2002 | Bartlett .................. | A61G 7/001 |
| | | | | 5/713 |
| 8,525,680 | B2 * | 9/2013 | Riley ..................... | A61G 7/005 |
| | | | | 5/713 |
| 10,905,249 | B1 * | 2/2021 | Saghiri ................ | A61B 5/6892 |
| 2009/0054752 | A1 * | 2/2009 | Jonnalagadda ........ | A61B 5/721 |
| | | | | 600/324 |

(Continued)

*Primary Examiner* — Fredrick C Conley
(74) *Attorney, Agent, or Firm* — Barnes & Thornburg LLP

(57)                ABSTRACT

A patient support apparatus comprises a plurality of load cells, a frame supported on the load cells, a mattress, a vibration sensor, and a control system. The mattress includes a plurality of inflatable zones positioned on the frame, the mattress and frame cooperating to direct any patient load through the mattress and frame to the load cells. The control system includes a controller operable to receive a separate signal from each of the plurality of load cells and the vibration sensor and process the signals to identify motion of the patient.

28 Claims, 10 Drawing Sheets

(56) References Cited

U.S. PATENT DOCUMENTS

| | | | |
|---|---|---|---|
| 2010/0152600 A1* | 6/2010 | Droitcour | A61B 5/7221 |
| | | | 600/534 |
| 2011/0068928 A1* | 3/2011 | Riley | A61B 5/024 |
| | | | 340/573.1 |
| 2012/0259245 A1* | 10/2012 | Receveur | A61G 7/0514 |
| | | | 5/616 |
| 2012/0259248 A1* | 10/2012 | Receveur | G16Z 99/00 |
| | | | 600/595 |
| 2014/0059781 A1* | 3/2014 | Lafleche | A61B 5/0205 |
| | | | 5/713 |
| 2023/0127922 A1* | 4/2023 | Receveur | A61G 7/0527 |
| | | | 705/3 |

* cited by examiner

46

36

38

46

42

18

48

HEAD ZONE

SEAT ZONE

THIGH ZONE

FOOT ZONE

BED SCALE NOISE COMPENSATION USING A REFERENCE TRANSDUCER

PRIORITY CLAIM

This application claims priority under 35 U.S.C. § 119(e) to U.S. Provisional Application No. 63/238,937, filed Aug. 31, 2021, which is expressly incorporated by reference herein.

BACKGROUND

The present disclosure relates to the use of sensors of a patient support apparatus, such as a hospital bed, for example, to detect patient motion and characterize the patient motion. More specifically, the present disclosure is directed to combining signals from load cells of a scale system and a force transducer to assess when there is no motion in order to measure a patient's weight and implement systems and methods to eliminate noise during patient weight measurements.

The use of load cells in patient support apparatuses, such as hospital beds, for example, to measure patient weight is known. Over time, approaches to using the information from the load cells to detect patient movement and to issue an alert or notification when the patient moves beyond a particular threshold have been developed. The use of load cells to make these determinations and inferences based on the motion is limited by the potential for external influences, such as the addition of equipment to the frame supported on the scale. When this is done, the existing information regarding the position of the patient is compromised as the weight distribution is changed unexpectedly.

The pressure sensors used to measure air pressure in zones of an inflatable mattress are used to control the inflation pressure in the zones to control the interface pressure experienced by a patient supported on the mattress. However, because of transient effects and lack of precision, air pressure sensors associated with mattress zones are not regularly used to measure patient information. The challenges of using air pressure sensors are exacerbated by the variability between the anthropometric characteristics of patients. People with completely different body types sometimes have similar weights. The variations in the surface area of bodies can vary the pressure and volume effects applied to inflatable zones. Still further, the variability in the construction of chambers in the zones makes every application necessary to characterize.

In addition, caregivers or visitors may intermittently apply pressure to the mattress, thereby changing air pressure measurements and the distribution of the weight on the frame. Motion algorithms generally rely on changes in the distribution of weight over multiple sensors to determine patient location and relative movement. These transient and external forces confound the algorithms used to determine patient movement and motion.

In some cases, it is important to determine patient movement relative to the patient support apparatus. Movement in this context means a change in position of the patient on the patient support apparatus, such as rolling over or moving toward an edge of a patient support apparatus to exit the patient support apparatus. In many instance a patient's baseline weight is used to determine if a patient is moving. Thus, it is important to accurately measure a patient's weight when there is no motion. In some cases, building noise may propagate through a patient support devices and confound measurements. It is imperative to identify and rectify any noise in the system to ensure accurate measurements.

Thus, there is a need to improve the approaches to measuring and characterizing patient motion and movement in real-time. Improving the identification of instances when there is no motion is important to accurately assess a patient's weight. Also, there is a need to implement systems and methods to eliminate noise during patient weight measurements.

SUMMARY

The present disclosure includes one or more of the features recited in the appended claims and/or the following features which, alone or in any combination, may comprise patentable subject matter.

According to a first aspect of the present disclosure, a patient support apparatus comprises a plurality of load cells, a frame supported on the load cells, a mattress including a plurality of inflatable zones positioned on the frame, the mattress and frame cooperating to direct any patient load through the mattress and frame to the load cells, a vibration sensor not supported on the load cells, and a control system including a controller, the controller operable to receive a separate signal from each of the plurality of load cells and the vibration sensor to monitor energy detected by each of the load cells, and the controller is further operable to process the signals to predict, based on transient changes in the signals, when there is no motion detected, to capture an offset with no motion content, and to automatically update a patient profile in a patient record.

In one embodiment of the patient support apparatus, the controller is operable to predict a minimum number of instances of no motion when there is motion. In some embodiments of the patient support apparatus, the controller uses a decision threshold to determine the probability of the motion, wherein if the probability of motion is under 0.05, the controller infers that there is no motion.

In one embodiment of the patient support apparatus, the controller is further operable to determine no motion, if there is no motion detected for a pre-determined time period. In some embodiments of the patient support apparatus, the controller is further operable to determine a total energy acting on the load cells as an average of total energy acting on the loads cells for about half the pre-determined time period. In other embodiments of the patient support apparatus, the pre-determined time period is about 5 continuous seconds.

In one embodiment of the patient support apparatus, the controller is able to detect any difference in patient weight in real time. In some embodiments of the patient support apparatus, any difference in the patient weight detected in real time by the controller is transmitted to one or more applications in one or more systems being used by the patient or the patient's caregiver. In one embodiment of the patient support apparatus, the detection of no motion accounts for noise in the patient support apparatus.

In one embodiment of the patient support apparatus, the controller further comprises adaptive filtering to mitigate the noise in the patient support apparatus. In some embodiments of the patient support apparatus, adaptive filtering comprises capturing and characterizing the noise when the patient in not supported on the patient support apparatus, translating the noise into filter parameters, designing a filter, applying and updating the filter parameters to the filter in real time.

In one embodiment of the patient support apparatus, a source of the noise is the floor on which the patient support apparatus is located and transmitted to the vibration sensor, the mattress, and the frame through a base of the patient support apparatus. In some embodiments of the patient support apparatus, a noise profile from the vibration sensor is created when the patient is not supported on the patient support apparatus and used to compensate for the noise from the floor on which the patient support apparatus is located.

In one embodiment of the patient support apparatus, the sensor is a force transducer or an accelerometer. In some embodiments of the patient support apparatus, the noise profile is translated into filter parameters for adaptive filtering of the noise in real time. In other embodiments of the patient support apparatus, the filter parameters are used in an adaptive filter to compensate for the noise from the floor on which the patient support apparatus is located.

In one embodiment, the patient support apparatus further comprises a plurality of air pressure sensors, each air pressure sensor measuring the pressure in a respective inflatable zone of the mattress According to a second aspect of the present disclosure, a system comprises a patient support surface including a plurality of inflatable zones, a plurality of load cells supporting the patient support surface, a vibration sensor not supported on the load cells, and controller operable to receive a separate signal from each of the plurality of load cells, to process the signals to predict, based on transient changes in the signals, when there is no patient motion, and to automatically update a patient weight in a patient record to reflect the characterization of the patient motion.

In one embodiment of the system, the controller is operable to predict a minimum number of instances of no motion when there is motion. In some embodiments of the system, the controller uses a decision threshold to determine the probability of the motion, wherein if the probability of motion is under 0.05, the controller infers that there is no motion. In other embodiments of the system, the controller is further operable to determine no motion, if there is no motion detected for a pre-determined time period.

In one embodiment of the system, the controller is further operable to determine a total energy acting on the load cells as an average of total energy acting on the loads cells for about half the pre-determined time period. In some embodiments of the system, the pre-determined time period is about 5 continuous seconds.

In one embodiment of the system, the controller is able to detect any difference in patient weight in real time. In some embodiments of the system, any difference in the patient weight detected in real time by the controller is transmitted to one or more applications in one or more systems being used by the patient or the patient's caregiver.

In one embodiment of the system, the detection of no motion accounts for noise in the system. In some embodiments of the system, the controller further comprises adaptive filtering to mitigate the noise in the system. In some embodiments of the system, adaptive filtering comprises capturing and characterizing the noise when the patient in not supported on the patient support surface, translating the noise into filter parameters, designing a filter, applying and updating the filter parameters to the filter in real time.

In one embodiment of the system, a source of the noise is the floor on which the system is located and transmitted to the vibration sensor, the mattress, and the frame through a base of the patient support apparatus. In some embodiments of the system, a noise profile from the vibration sensor is created when the patient is not supported on the patient support apparatus and used to compensate for the noise from the floor on which the patient support apparatus is located.

In one embodiment of the system, the sensor is a force transducer or an accelerometer. In some embodiments of the system, the noise profile is translated into filter parameters for adaptive filtering of the noise in real time. In some embodiments of the system the filter parameters are used in an adaptive filter to compensate for the noise from the floor on which the system is located.

In one embodiment, the system further comprises a plurality of air pressure sensors, each pressure sensor measuring the pressure in a respective inflatable zone of the patient support surface.

According to a third aspect of the present disclosure, a method of updating weight of a person on a patient support apparatus comprising an inflatable mattress having multiple inflatable zones, the method comprises the steps of, monitoring signals from a plurality of load cells, the plurality of load cells supporting inflatable mattress, monitoring signals from a vibration sensor not supported on the load cells, monitoring the energy detected by each of the load cells, processing the signals from the load cells to identify any motion, upon detection of no motion, capturing an offset with no motion content, and automatically updating a record associated with the particular person to reflect the person's weight.

In one embodiment of the method, processing the signals from the load cells to identify any motion comprises a controller that is operable to predict a minimum number of instances of no motion when there is motion. In some embodiments of the method, the method further comprises the controller using a decision threshold to determine the probability of motion, wherein if the probability of motion is under 0.05, the controller infers that there is no motion. In other embodiments of the method, the method further comprises the controller operable to determine no motion, if there is no motion detected for a pre-determined time period.

In one embodiment of the method, the method further comprises the controller determining a total energy acting on the load cells as an average of total energy acting on the loads cells for about half the pre-determined time period. In some embodiments of the method, the pre-determined time period is about 5 continuous seconds.

In one embodiment of the method, the method further comprises the controller operable to detect any difference in patient weight in real time. In some embodiments of the method, any difference in the patient weight detected in real time by the controller is transmitted to one or more applications in one or more systems being used by the patient or the patient's caregiver.

In one embodiment of the method, the detection of no motion accounts for noise in the patient support apparatus. In some embodiments of the method, a source of the noise is the floor on which the patient support apparatus is located and transmitted to the frame supported on the load cells.

In one embodiment of the method, the controller further comprises adaptive filtering to mitigate the noise in the patient support apparatus. In some embodiments of the method, adaptive filtering comprises capturing and characterizing the noise when the patient in not supported on the patient support apparatus, translating the noise into filter parameters, designing a filter, applying and updating the filter parameters to the filter in real time In one embodiment of the method, the patient support apparatus comprises a source of the noise is the floor on which the patient support apparatus is located and transmitted to the vibration sensor. In some embodiments of the method, the noise from the floor propagates to the vibration sensor, and the inflatable mattress, through a base of the patient support apparatus, and a noise profile from the vibration sensor is created when the patient is not supported on the patient support apparatus and used to compensate for the noise from the floor on which the patient support apparatus is located. In some embodiments of the method, the sensor is a force transducer or an accelerometer. In other embodiments of the method, the noise profile is translated into filter parameters for adaptive filtering of the noise in real time. In some embodiments of the method, the filter parameters are used in an adaptive filter to compensate for the noise from the floor on which the patient support apparatus is located.

In one embodiment of the method, the method further comprises monitoring signals from a plurality of pressure sensors, each pressure sensor providing a signal indicative of the pressure in a respective inflatable zone Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
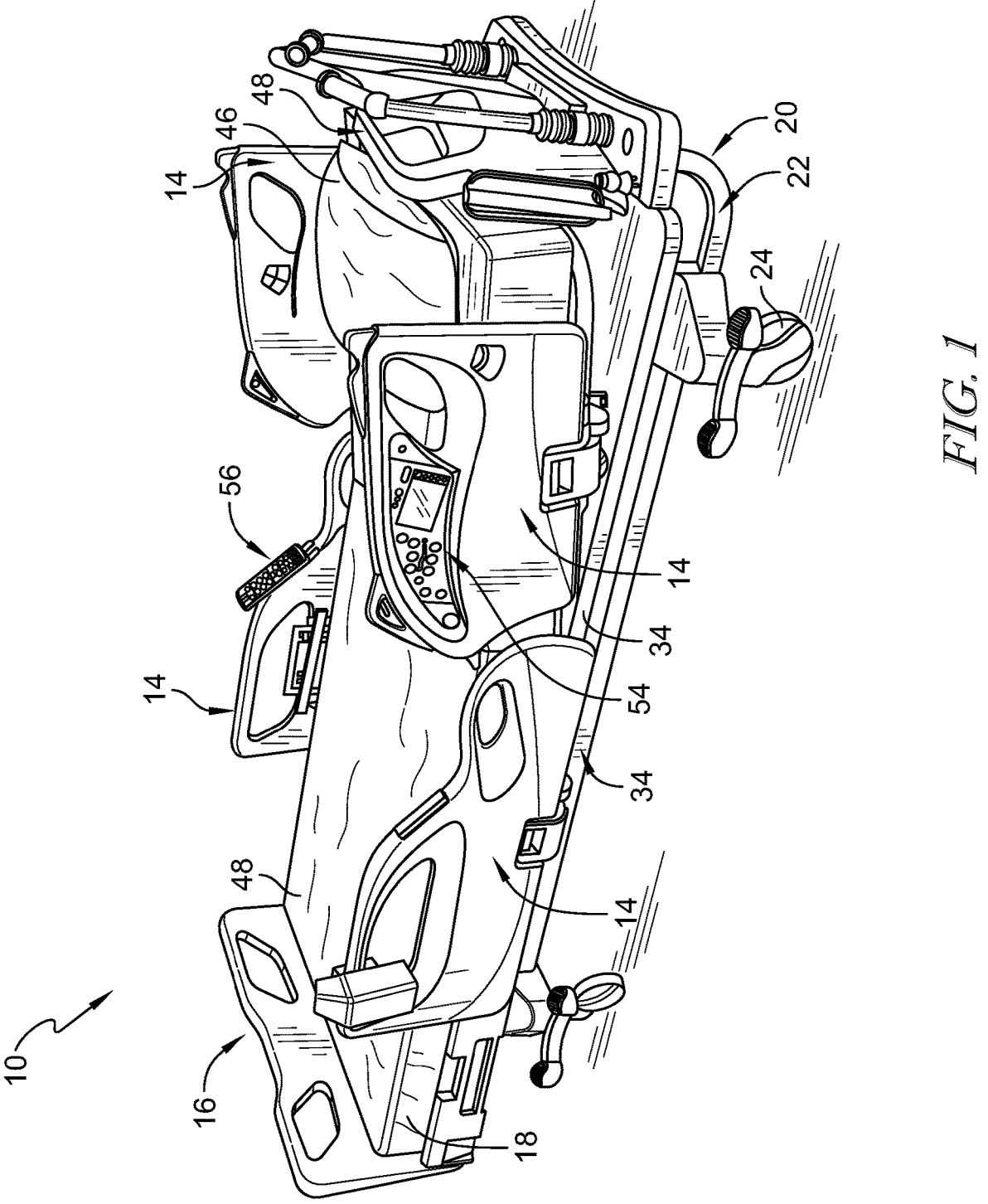
FIG. 1 is a perspective view of a patient support apparatus including a control system operable to measure signals from a plurality of sensors and process those signals according to the present disclosure.
Figure 5:
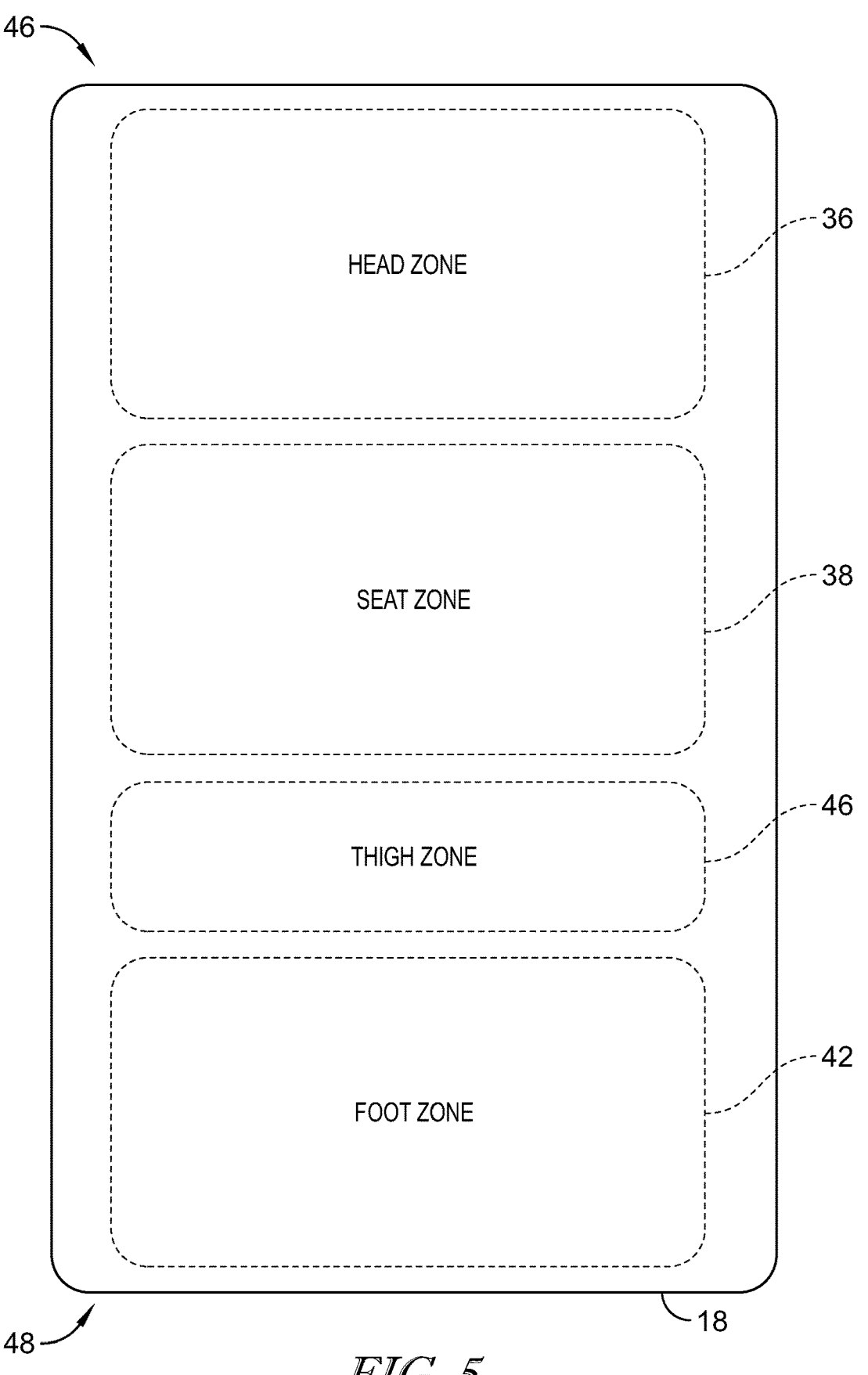
FIG. 5 is a diagrammatic representation of a mattress of the patient support apparatus of FIG. 1, the mattress including multiple inflatable zones.

An illustrative patient support apparatus 10 embodied as a hospital bed is shown in FIG. 1. The bed 10 of FIG. 1 has a frame 20 which includes a base frame 22 supported on casters 24. The stationary base frame 22 further supports a weigh frame 30 that an adjustably positionable mattress support upper frame 34 supporting a mattress 18. As shown in FIG. 5, the illustrative mattress 18 is an inflatable patient support surface which includes inflatable zones including a head zone 36, a seat zone 38, thigh zone 40, and a foot zone 42. The bed 10 further includes a headboard 12 at a head end 46 of the bed 10, a footboard 16 at a foot end 48 of the bed 10, and a movable siderails 14 coupled to the upper frame 34 of the bed 10. The bed 10 also includes a user interface 54 positioned on one of the siderails 14. The bed 10 of the embodiment of FIG. 1 is conventionally configured to adjustably position the upper frame 34 relative to the base frame 22 to adjust the position of a patient supported on the mattress 18.

Conventional structures and devices may be provided to adjustably position the upper frame 34, and such conventional structures and devices may include, for example, linkages, drives, and other movement members and devices coupled between base frame 22 and the weigh frame 30, and/or between weigh frame 30 and upper frame 34. Control of the position of the upper frame 34 and mattress 18 relative to the base frame 22 or weigh frame 30 is controlled, for example, by a patient control pendant 56 or user interface 54. The upper frame 34 may, for example, be adjustably positioned in a general incline from the head end 46 to the foot end 48 or vice versa. Additionally, the upper frame 34 may be adjustably positioned such that the head section 44 of the mattress 18 is positioned between minimum and maximum incline angles, e.g., 0-65 degrees, relative to horizontal or bed flat, and the upper frame 34 may also be adjustably positioned such that a seat section (not shown) of the mattress 18 is positioned between minimum and maximum bend angles, e.g., 0-35 degrees, relative to horizontal or bed flat. Those skilled in the art will recognize that the upper frame 34 or portions thereof may be adjustably positioned in other orientations, and such other orientations are contemplated by this disclosure.

Figure 2:
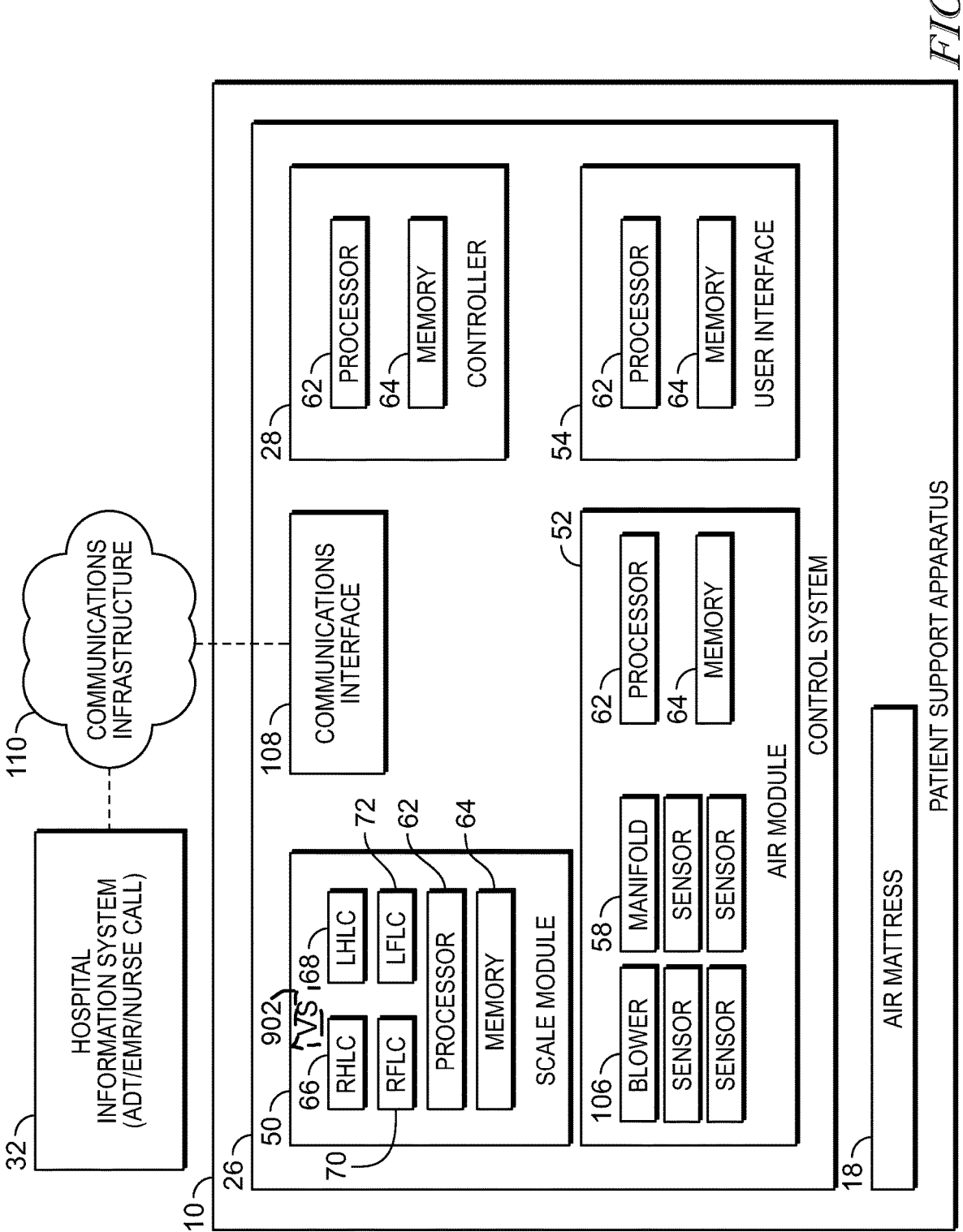
FIG. 2 is a block diagram of a portion of the control system of the patient support apparatus of FIG. 1.

In one illustrative embodiment shown diagrammatically in FIG. 2, the bed 10 has a control system 26 that includes a controller 28, a scale module 50, an air module 52, and the user interface 54. In the illustrative embodiment each of the controller 28, scale module 50, air module 52, and user interface 54 includes a processor 62 and a memory device 64. The processor 62 and memory device 64 are shown with respect to the controller 28, the scale module 50, the air module 52, and the user interface 54. The memory device 64 includes instructions that, when executed by the processor 62, cause the processor 62 to perform functions as associated with the particular one of controller 28, scale module 50, air module 52, and user interface 54. The components of the control system 26 communicate amongst themselves to share information and distribute the functions of the bed 10. The processor 62 of each of the controller 28, scale module 50, air module 52, and user interface 54 is also operable, based on instructions from the memory device 64, to communicate with the others of the controller 28, scale module 50, air module 52, and user interface 54 using a communications protocol. It should be understood that the term processor here includes any microprocessor, microcontroller, processor circuitry, control circuitry, preprogrammed device, or any structure capable of accessing the memory device and executing non-transient instructions to perform the tasks, algorithm, and processed disclosed herein. In the illustrative embodiment, the control system 26 employs a conventional controller area network (CAN) for communications between subsystems, but it should be understood that any of a number of networking and communications solutions could be employed in the control system 26.

Figure 3:
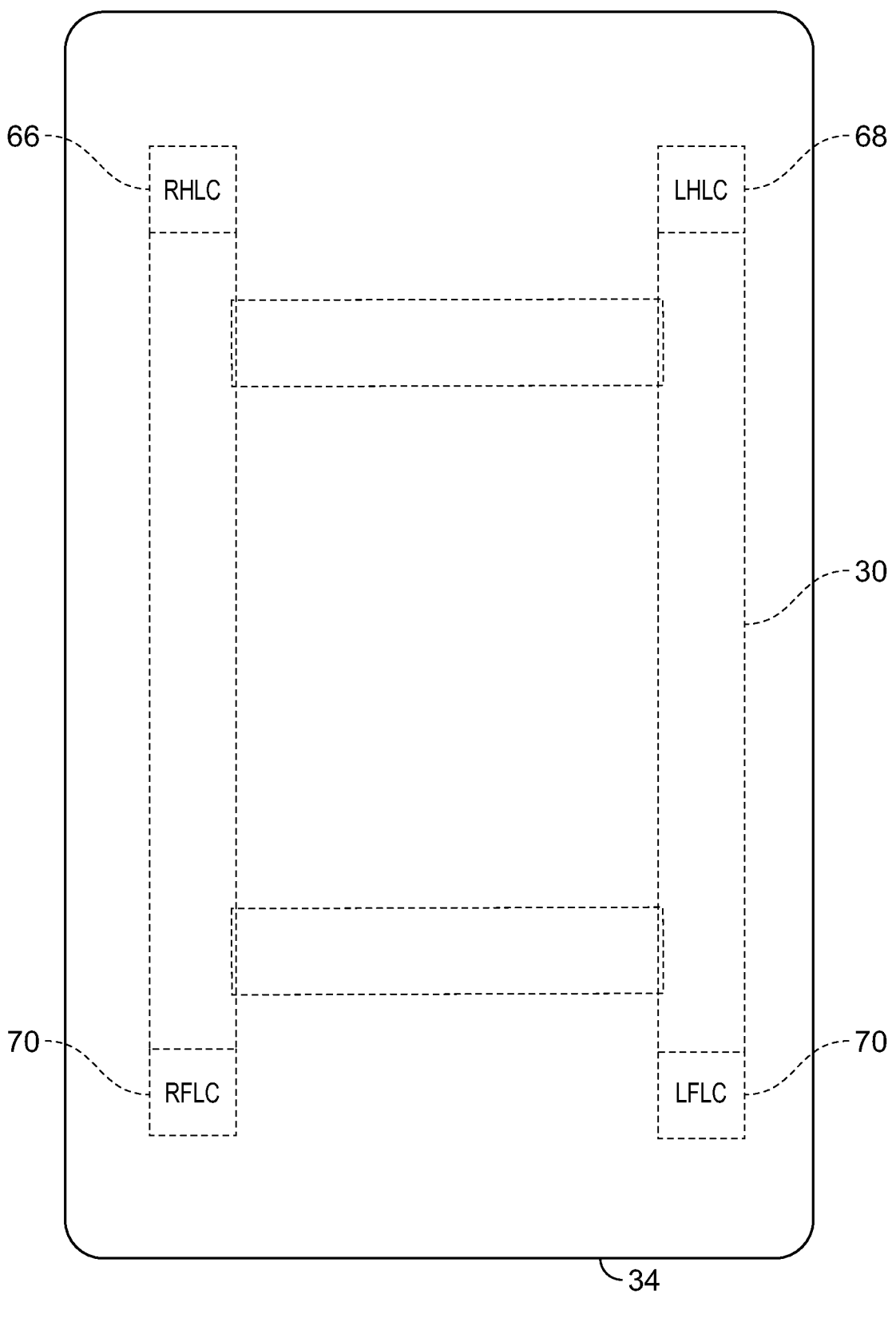
FIG. 3 is a diagrammatic illustration of the interaction between a first frame of the patient support apparatus of FIG. 1 and a second frame supported on load cells supported from the first frame.
Figure 4:
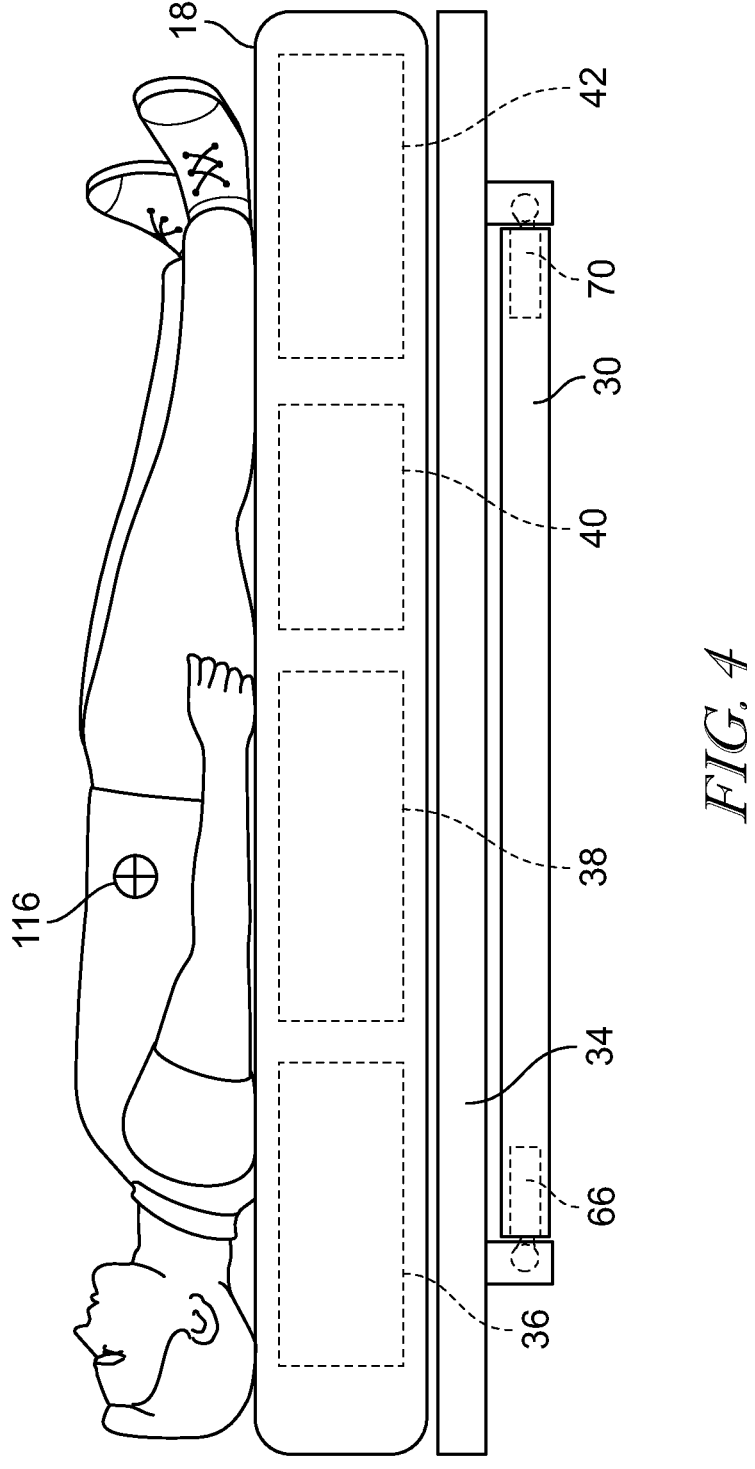
FIG. 4, is a side view of a portion of the patient support apparatus of FIG. 1 showing a first frame supported on load cells supported on a second frame, the load cells supporting all of the load of the first frame.

As shown in FIG. 3, the bed 10 includes four load cells 66, 68, 70, and 72. To determine a weight of a patient supported on the mattress 18, the load cells 66, 68, 70, and 72 are positioned between the weigh frame 30 and the upper frame 34 as illustrated in FIGS. 3 and 4. Each load cell 66, 68, 70, 72 is configured to produce a signal indicative of a load supported by the respective load cell 66, 68, 70, 72 from the upper frame 34 relative to the weigh frame 30. Some of the structural components of the bed 10 will be designated hereinafter as "right", "left", "head" and "foot" from the reference point of an individual lying on the individual's back on the mattress 18 with the individual's head oriented toward the head end 46 of the bed 10 and the individual's feet oriented toward the foot end 48 of the bed 10. Following this convention, the load cell 66 is designated as the right head load cell (RHLC) in the figures to represent that the load cell 66 is positioned at the right side of the bed 10 at the head end 46. The load cell 68 is designated at the left head load cell (LHLC), the load cell 70 is designated as the right foot load cell (RFLC), and the load cell 72 is designated left foot load cell (LFLC), each following the same convention.

As shown in FIG. 2, the scale module 50 includes a processor 62 that is in communication with each of the respective load cells 66, 68, 70, and 72 and operable to process the signals from the load cells 66, 68, 70, and 72. The memory device 64 is also utilized by the controller 28 to store information corresponding to features and functions provided by the bed 10.

A weight distribution of a load among the plurality of load cells 66, 68, 70, and 72 may not be the same depending on variations in the structure of the bed 10, variations in each of load cells 66, 68, 70, and 72 and the position of the load on the mattress 18 relative to the particular load cell 66, 68, 70, or 72. Accordingly, a calibration constant for each of the load cells 66, 68, 70, and 72 is established to adjust for differences in the load cells 66, 68, 70, and 72 in response to the load borne by each. Each of the load cells 66, 68, 70, and 72 produces a signal indicative of the load supported by that load cell 66, 68, 70, or 72. The loads detected by each of the respective load cells 66, 68, 70, 72 are adjusted using a corresponding calibration constant for the respective load cell 66, 68, 70, 72. The adjusted loads are then combined to establish the actual weight supported on the bed 10. In the present disclosure, the independent signal from each of the load cells 66, 68, 70, 72 is used to draw inferences about the movement and motion of the patient.

The air module 52 is the functional controller for the mattress 18 and includes a processor 62 and a memory device 64. The processor 62 is in communication with a blower 106, a manifold 58, and an air pressure sensor assembly 60. The air module 52 is a conventional structure with the manifold 58 operating under the control of the processor 62 to control the flow of air from the blower 106 into and out of the head zone 36, seat zone 38, thigh zone 40, and foot zone 42 to control the interface pressure experienced by the patient supported on the mattress 18. The sensor assembly 60 includes separate sensors for measuring the air pressure in each of the head zone 36, seat zone 38, thigh zone 40, and foot zone 42. The pressure sensor assembly includes a head zone sensor 82, a seat zone sensor 84, a thigh zone senor 86, and a foot zone sensor 88. While signals from the sensors 82, 84, 86, and 88 are used to control the pressure in the respective zones, applying the principles of the present disclosure, the signals are also useful in making inferences regarding patient movement and, when used synergistically with the information gleaned from the signals from the load cells 66, 68, 70, and 72, provide a more fulsome and accurate analysis of patient movement and/or any motion associated with the patient support apparatus 10.

Through an empirical study that included real-time data collection from video observation of test subject patients synchronized with signals from load cells 66, 68, 70, and 72 of the scale module 50 of the bed 10 supporting the test subject patients, the types of motion on the bed 10 were classified into one of three types: lateral patient motions (LPMs); vertical or self-offloading patient movements (SOs); or non-patient motion artifacts (NPMAs). There were also observations that indicated that signals from load cells 66, 68, 70, and 72 varied when there was no patient movement. These artifacts were designated as non-movements (NMs). Permutations of these categories, called "complex movements", also including further categorization into combinations including different directionality of the simple movements was also established.

Like all biomedical sensing systems, error can be introduced when the signals from the load cells of a bed 10, such as load cells 66, 68, 70, and 72 to sensor output is affected by various sources of noise. Some sources of noise, such as electrical or stray environmental noise can be mitigated through robust design. However, there may be mechanical noise coming from the floor on which the patient support apparatus 10 is physically located and the noise may propagate up through the frame and into the load cells 66, 68, 70, and 72. The noise may be coming from inside or outside of the building in which the patient support apparatus 10 is placed. The noise may be due to devices such as HVAC units, server coolers, or other machinery.

Figures 8A, 8B, 8C:
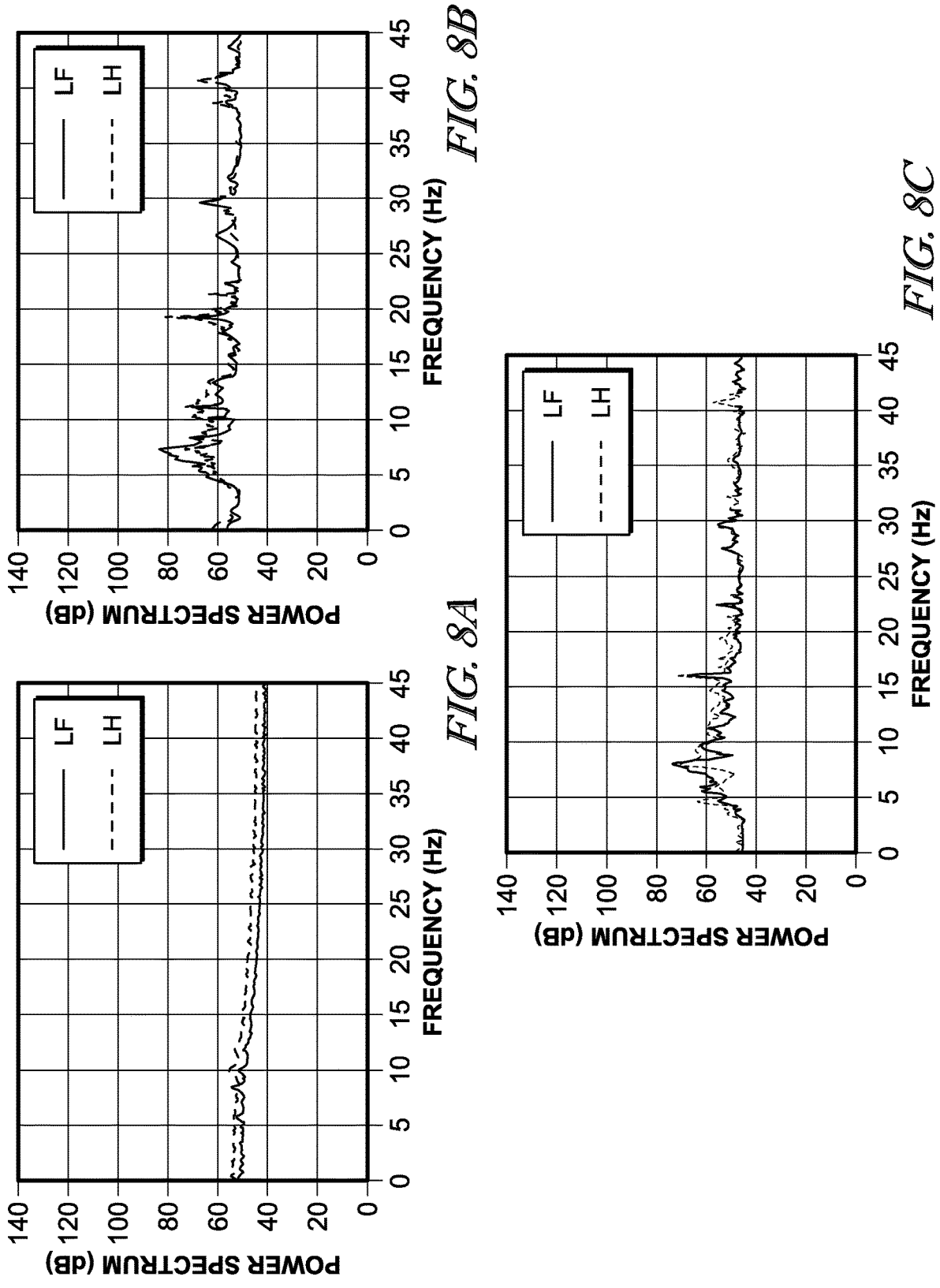
FIG. 8A is a spectral density function plot of a bed in a lab with vibration isolating structures.
FIG. 8B is a spectral density function plot of a bed in a lab environment.
FIG. 8C is a spectral density function plot of a bed in a hospital in a hospital setting.

Spectral density function (SDF) plots of samples taken from beds 10 placed in three different locations, first in the basement of a lab in Georgia Institute of Technology (FIG. 8A), a second in the $3^{rd}$ floor lab space in Cary, NC (FIG. 8B), and a third at a hospital location in University of Virginia (FIG. 8C) are shown in FIG. 8. It is worth noting that the bed 10 in Georgia Institute of Technology was in the basement of a building and in a room that has a "floating floor" to purposely isolate vibrations during experiments.

Figure 9:
FIG. 9 is a schematic showing a reference load cell in a patient support apparatus that is not connected to the weigh frame and accounts for building noise.

When designing a scale system using load cells 66, 68, 70, and 72, it is important that these noise sources not affect the accuracy of the system. Spurious noise can "push up" the forces so that more load/weight is measured than what is actually present. Simple low-pass filters may mitigate these sources of noise, but since the sources of the noise can vary, it is important for the patient support apparatus 10 to adapt to the environment that it is in. In one embodiment, adaptive filtering may be used to mitigate the noise. Adaptive filtering is the process of subtracting noise from what is measured, which is typically noise plus the signal of interest. In other embodiments, noise in the system may be filtered by using one or more force transducers in the patient support apparatus 10. The patient support apparatus 10 may have a force transducer that is not subjected to the patient's forces, while being subjected to the any noise that is conducted from the floor on which the patient support apparatus 10 is resting or any building noise in the building comprising the patient support apparatus 10. The scale module may comprise a vibration sensor embodied as a secondary load cell or force transducer 902, as shown in FIG. 9. The processor 62 in the scale module 50 may be in communication with a secondary load cell or force transducer 902 in addition to the load cells 66, 68, 70, and 72 and may be operable to process the signals from the load cells 66, 68, 70, 72, and 902. The memory device 64 may also be utilized by the controller 28 to store information corresponding to the load cells 66, 68, 70, 72, and 902.

According to the present disclosure, the scale module 50 and air module 52 of the bed 10 are used for measuring the motions of a patient that occupies the bed 10. Referring to FIG. 4, a diagrammatic side view of a patient supported on the mattress 18 and frame 34 with the load of the patient being borne by the inflated zones 36, 38, 40, and 42 and passed through the mattress to the frame 34 to the load cells 66, 68, 70, and 72 supported from the weigh frame 30. As seen in FIG. 4, in a static condition, the patient's weight is appropriately distributed over the inflated zones 36, 38, 40, and 42. Each of those zones 36, 38, 40, and 42 are inflated to a target pressure based on the patient's weight detected by the scale module 50 and the expected distribution of the patient. The scale module 50 and air module 52 of the bed 10 may also account for any system based noise by processing data from the secondary load cell or force transducer 902.

It is not always possible to mitigate human-caused forces that are imparted to the load cells 66, 68, 70, and 72 that are not generated from solely the patient themselves, i.e., non-patient motion artifacts (NPMA). When NPMAs occur, they are typically much greater in motion magnitude than patient motions. Failure to acknowledge and adjust for the presence of these NPMA results in an inaccurate inference of mobility, self-directed motion, etc. to bias towards patients having much more mobility than they actually have. To determine the difference between patient movements, in particular, to determine the difference between self-offloading patient movements (SOs) and non-patient motion artifacts (NP-MAs), patient weight must be determined and/or measured in real-time.

Patient weight can decrease with time, for instance, patient weight can change after urinations, after a meal, or when the patient is being given any intravenous flow. The use of the signals from the load cells of a bed, such as load cells 66, 68, 70, and 72 to determine the equivalent centroid of vertical load supported by the load cells 66, 68, 70, and 72 is known. This centroid/center-of-gravity (CG) approach is used to infer some patient motion. Through empirical analysis, a determination of motion in the x/y plane of a range of speeds and magnitudes of motion that are associated with patient motions has been determined. Thus, this allows for the detection of lateral patient motions (LPMs), which are, by definition, detected patient motions which have no vertical component.

Any lateral movement will cause the center of gravity of the patient on the bed 10 to change during a unit-time interval, proportionally to ratio of the displacement of the amount of mass moved to the amount of mass that remained stationary. Due to this, this feature is self-normalized by patient weight. Thus, it is important to continuously monitor the patient's weight. Note that CG movement in the x and y axis is merged by typical vector addition and the directionality is ignored to establish a factor called CGspeed. It is understood that both patient and non-patient movements will cause the CG to move, for these reasons, and the classifiers and inference models discussed below, any motion that imparts its force to the weigh frame 30 is considered to be a motion. The present disclosure is directed to having a practical and accurate measurement of a patient's weight when there is no motion detected.

In a first approach, the patient and the bed 10 are treated as a closed system. The total energy of the closed system will be constant and conserved over time of typical patient movements. Any energy that is created by the patient as a result of them moving does not change the overall loading of all four load cells 66, 68, 70, and 72, but simply changes the proportion the total load that each load cell 66, 68, 70, or 72 is carrying at any given time. There is no total gain of loads, the loads simply shift around the four load cells 66, 68, 70, and 72 as the patient moves laterally.

In contrast, when a caregiver pushes or pulls on the patient or bed 10 (a NPMA), the closed-system is corrupted by an external energy source and the net load on the load cells 66, 68, 70, and 72 increased or decreased. This is the case for both transient touches of the bed 10, such as when a person hugs the patient, and in sustained touches of the bed 10, such as when a caregiver leans on bed 10 while doing long procedure. In either case, an additional load is introduced to the load cells 66, 68, 70, and 72 resulting in a material change from the sum of the loads on each load cell 66, 68, 70, and 72 when the transient load is applied to the bed 10. The value of the transient load, designated as total transient load (TTL) is calculated by subtracting from the total load measured by the load cells 66, 68, 70, and 72, the closed-system load measured before the transient event; the closed-system load which is effectively the patient's static weight, designated as the DC sum of beams (DC SB) which may be determined using known techniques, such as that disclosed in U.S. Pat. No. 10,054,479 titled "BED WITH AUTOMATIC WEIGHT OFFSET DETECTION AND MODIFICATION," which is incorporated herein for the disclosure of monitoring and updating a patient load to establish a static patient weight, DCSB.

For the purposes of this disclosure, DCSB is used interchangeably with the patient's weight. Once the DCSB or patient weight is established, a simple threshold can be tested to determine whether a TTL is a NPMA or not. The DCSB or patient weight before the motion must have been determined. Thus, the patient weight must be regularly captured in-between motions. An algorithm must be designed to capture this value in-between motions. The units here are forces, measured in kg, also called kg-force. As part of the test of the threshold, an oscillation in the location of the CG and an effective return of the TTL to zero can be considered to confirm the transient nature of the load to help confirm that the event is a TTL. However, there is an exception to this simple approach. Relying just on threshold-ing TTL moment-by-moment is confounded by self-offloading patient movements (SOs). SOs are large vertical shifts that are an artifact of a patient quickly lifting their core body up using the strength in his legs or arms and then returning to a starting or near starting position. These self-movements cause large momentary changes in TTL and may appear to be an NPMA. Although SOs can cause momentary large shifts from the patient's weight in the closed system, appearing to break it, the closed system is not broken if the response of the system through the entire duration of the motion is considered.

To study the type, frequency of occurrence, and behavior of non-patients causing NPMA events, video data was recorded concurrently with recording bed data (load cell, pressure sensor from surface, bed data such as side rail status, etc.). The video data was synchronized in time with the bed data. To establish characterization criteria, an empirical study using the synchronized video and signal from load cells 66, 68, 70, and 72 capture approach discussed above was implemented to gather a mixture of human-generated and human-surrogate test movements were performed. In some embodiments, signal from the secondary load cell or force transducer 902 may be processed to account for system based noise. Taking care to vary parameters such as motion speed and magnitude of both patient and NPMA movements, and introducing variability such as different body shapes and strengths in the case of the human subjects, a representative data sample was developed. In the case of the human subjects, three subjects were used a ten-year-old male, 44.5 kg, a fourteen-year-old female, 60 kg, and a forty-year-old male, 101 kg.

Using the empirically generated test data, an approach was developed to model the absolute total transient load (ATTL), which is defined as:

$$ATTL=|[\Sigma(RHLC,LHLC,RFLC,LFLC)-DCSB]/DCSB \quad (EQ. 1)$$

Where RHLC, LHLC, RFLC, and LFLC are the values in kg, of the four load cells 66, 68, 70, and 72 and DCSB, which is defined above. This approach provides an absolute value of the TTL, recognizing that transient loads may also unload the weigh frame 30 in some situations.

The DCSB or the patient's weight needs to be updated often for use in the absolute total transient load (ATTL) calculation. This is because there are many instances when the patient weight cannot be assumed to be the same weight as was captured by the caregiver when using the scale system. For example, simply picking up an object from an over-bed table may cause an offset in the DCSB. Objects may be handed to the patient, and/or objects may be quasi-permanently attached on the weigh frame supporting the patient (e.g., SCD boots) or be placed on the mattress supporting the patient (e.g., additional pillows). Additionally the caregiver may not always take an initial patient weight. It is also important that when updating the patient's weight, the system accounts for any spurious noise. In some embodiments, the system may account of such noise by using one or more force transducers 902 in the patient support apparatus such as the bed 10 or by implementing algorithms such as adaptive filtering.

DCSB cannot be the basis to determine the need to capture a new DCSB. Thus, for the purposes of capturing a new DCSB, a DCSB algorithm is implemented as discussed below. CGspeed and/or SumbeamsSD may be used in the implementation of the DCSB algorithm.

The conservation of energy theory is modeled using an integral approach and taking the absolute value of the integral as shown below.

$$centInt=|\int_L^{-L}[(sum(RHLC,LHLC,RFLC,LFLC)-DCSB)/DCSB]| \quad (EQ. 2)$$

CGspeed is calculated as follows.

$$CGspeed = \frac{\left(\sqrt{\Delta CGx^2 + \Delta CGy^2}\right)}{t} \quad (EQ. 3)$$

$$CGx = X*(LHLC + LFLC)/sum(RHLC, LHLC, RFLC, LFLC) \quad (EQ. 4)$$

$$CGy = Y*(RHLC + RFLC)/sum(RHLC, LHLC, RFLC, LFLC) \quad (EQ. 5)$$

Where t, is the time interval over which the change in the position of the CG moves and where X is the distance between the left load cells 68, 72 and the right load cells 66, 70, and Y is the distance between head load cells 66, 68 and the foot load cells 70, 72.

While CGSpeed may be sensitive to motion in the x-y plane occurring at the moment, SumBeamsSD may be sensitive to impulses in the z dimension.

$$SumBeamsSD=stdev(sum(RH,LH,LF,RH)) \quad (EQ. 6)$$

Although it appears that patient motion is predicted by one variable, and NPMA/non-NPMA is determined by two, an approach that would serialize classifiers by determining if there is any motion (patient or non-patient) and pass that data into the classifier that determines the presence of NPMA vs. non NPMA is implemented.

A binary logistic regression is used to determine a simple threshold that could easily be deployed in an embedded system. Due to the binary shape of a sigmoid (shape that is used in logistic regression), this equation can represent a boundary in two-dimensional feature space, where the third dimension is the probability of motion. It can be said that any data point above this line will be part of the motion group and any data point below this line will be a part of the no-motion group. A 10-times K-folds cross-validation with an 80/20 ratio split of the training from the validation data is performed. The data is balanced in the classes 0=no motion and 1=motion as follows, where each "count" corresponds to a single $10^{th}$ second long "moment" where there is motion or no motion.

An AUC-ROC curve is prepared to score the performance of the motion classifier classification approach applied at various thresholds for TPR vs. FPR. The validation test resulted in an ROC AUC of 0.99, which is a near-perfect classifier. For this motion detection model, using a threshold of 0.5, 99% of the time true motion is detected and 88% of the time no motion is detected when there is truly is some motion.

The coefficients from this model describes the relationship between a predictor features and the probability of motion and are shown as the betas below:

$$Pm = \frac{e^y}{1 + e^y} \quad (EQ. 7)$$

where $y = \beta_1 x_1 + \beta_2 x_2 + \beta_0$ $\beta_1 = 8.6018$, $x_1 = CGspeed$, $\beta_2 = 253.46103$, $x_2 = SumBeamsSD$, $\beta_0 = -7.60734$ Where Pm is the probability there is a motion. In one embodiment, when Pm is over than 0.5, it may be inferred that there is motion.

Table 1 illustrates a confusion matrix when the threshold of probability of false positives and false negatives are balanced at 0.5.

TABLE 1

| | Predicted No motion | Predicted Motion |
|---|---|---|
| True No Motion | 6241 | 32 |
| True Motion | 292 | 3614 |

It is important to identify no motion and to do so very specifically. The specificity of detecting no motion is more important than the sensitivity of detecting all instances of no motion. It is important to identify an instance of no motion when they is truly no patient movement and no NPMA, so that an offset can be captured with no motion content. It is important to identify as few instances of predicting no motion when in fact there is motion.

Table 2 illustrates the change in the confusion matrix, when the threshold is changed to 0.05. The number of predicted no motion instances when there is motion decreases from 292 to 83. This is close to optimal. Thus, in some embodiments, when the probability of motion is under 0.05, no motion may be inferred, and the DCSB or the patient weight may be recaptured.

TABLE 2

|  | Predicted No motion | Predicted Motion |
|---|---|---|
| True No Motion | 4857 | 1416 |
| True Motion | 83 | 3823 |

In some embodiments, additional criterion may be used to determine no motion prior to capturing the DCSB or the patient weight. The additional criteria may comprise detection of no motion for at least a time period of about 5 seconds. In some embodiments, an averaged total force for a few seconds such as for about 2 to about 5 seconds may be captured. In some embodiments, the captured value may be the average force during half of the required time period of detecting no motion, i.e. about 2.5 seconds.

If motion is predicted, the motion is further classified as NPMA, LPM, or SO. The following equation represents a vertical line indicating that any data point to the right side will be NPMA.

$$Pn = \frac{e^y}{1 + e^y} \qquad \text{(EQ. 8)}$$

where $y = \beta_1 x_1 + \beta_2 x_2 + \beta_0$ $\beta_1 = 2.729$, $x_1 = centintAbs$, $\beta_0 = -4.38$ Where centintAbs is the absolute value of centInt and Pn is the probability there is a NPMA event. In one embodiment, when Pn is over than 0.5, it may be inferred that the motion is a NPMA.

Figure 6:
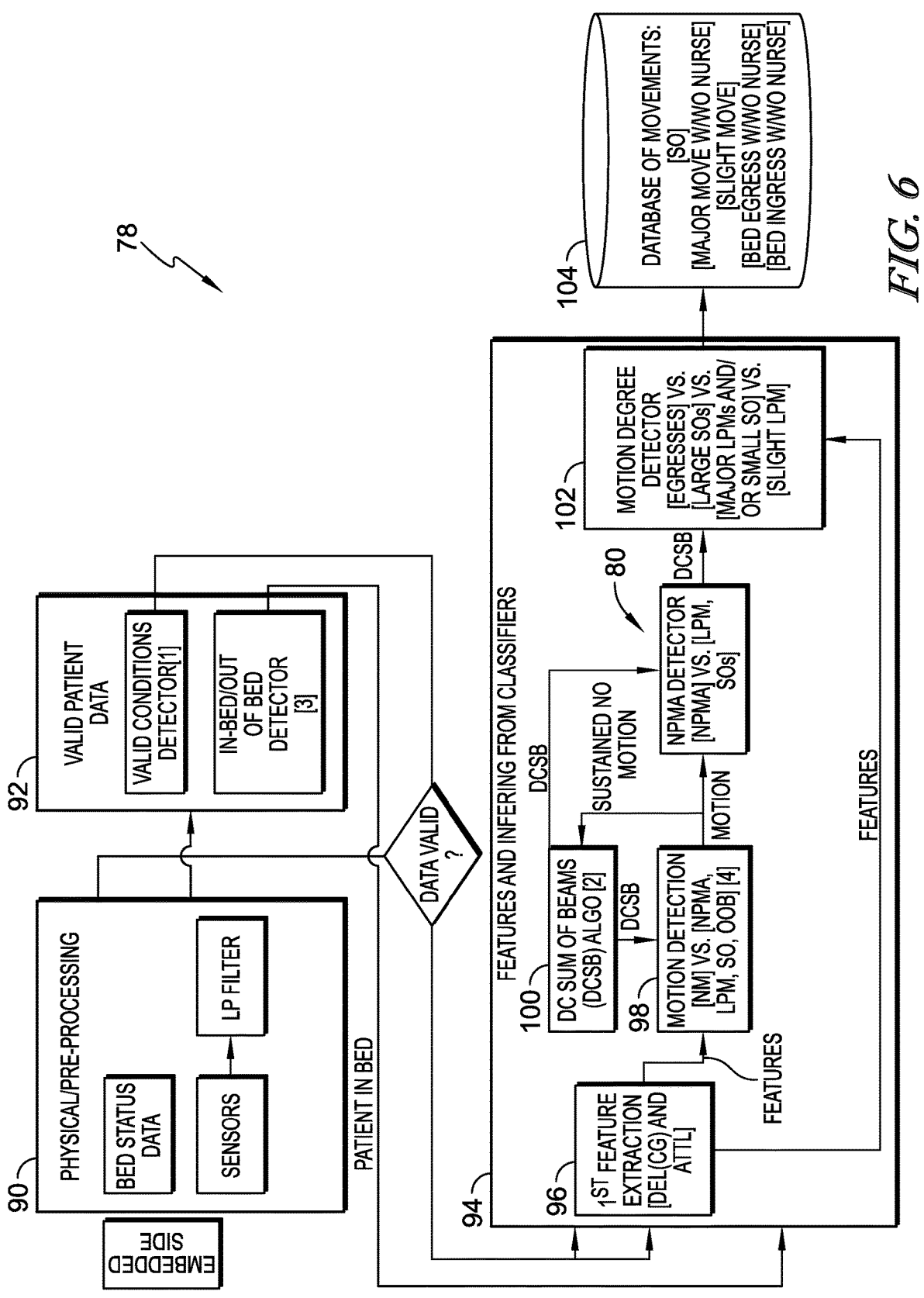
FIG. 6 is a diagrammatic representation of an algorithm for characterizing sensor signals from the patient apparatus of FIG. 1.

Having successfully established that the features under study could be extracted and applied with confidence in an inference model, a generalized algorithm 78 for processing sensor data from existing sensors from a bed 10 is developed as shown in FIG. 6. At a pre-processing step 90, bed status data and sensor data are pre-processed with sensor data being filtered, such as through low-pass filter. Additional testing is confirmed at step 92 where data being transferred into an inference engine 94 is validated. At step 92, validation include a determination that sensor data being received is consistent with the environment of the bed 10 and patient. In some examples, information may be received from a hospital information system 32 which indicates an expected sensor signal range. For example, validation may test the DCSB against the weight of the patient in the hospital information system 32 to validate that the signals from the load cells 66, 68, 70, 72 are reasonable. The hospital information system 32 may include an admission/discharge/transfer (ADT) management system, an electronic medical records system, or a nurse call system. Each of these units of the hospital information system 32 may regularly communicate with others of the systems or may be standalone systems. The validation step 92 may also use other sensors to confirm that a patient is in the bed 10 and generating meaningful data to confirm the validity of the algorithm 78 in real time.

The filtered data is provided to the inference engine 94 where at step 96 a first feature extraction is conducted. From the example above, a first feature is extracted to confirm whether there is a threshold state, such as motion or no motion, as described above.

In other embodiments, other first features may be extracted as the first step in a serial classification approach. Upon extraction of the first feature, the serial classification approach is continued with the features extracted in step 96 advanced to step 98 where baseline data is tested against an extracted first feature to determine whether a threshold has been met that is indicative of motion. If no motion is detected, the algorithm 78 loops at step 98 until motion is identified and classification can be conducted. Furthermore, if no motion is detected, the algorithm 78 implements the DCSB algorithm to determine the patient weight at step 100. The DCSB or the patient weight is further used to distinguish patient movement from NPMA.

Still further, it is contemplated that if the controller 28 detects any change in patient weight, the controller 28 may communicate that change through the communications interface 108 to the hospital information system 32 for action by caregivers. Similarly, the controller 28 may communicate any change in patient weight to the user interface 54.

Figure 7:
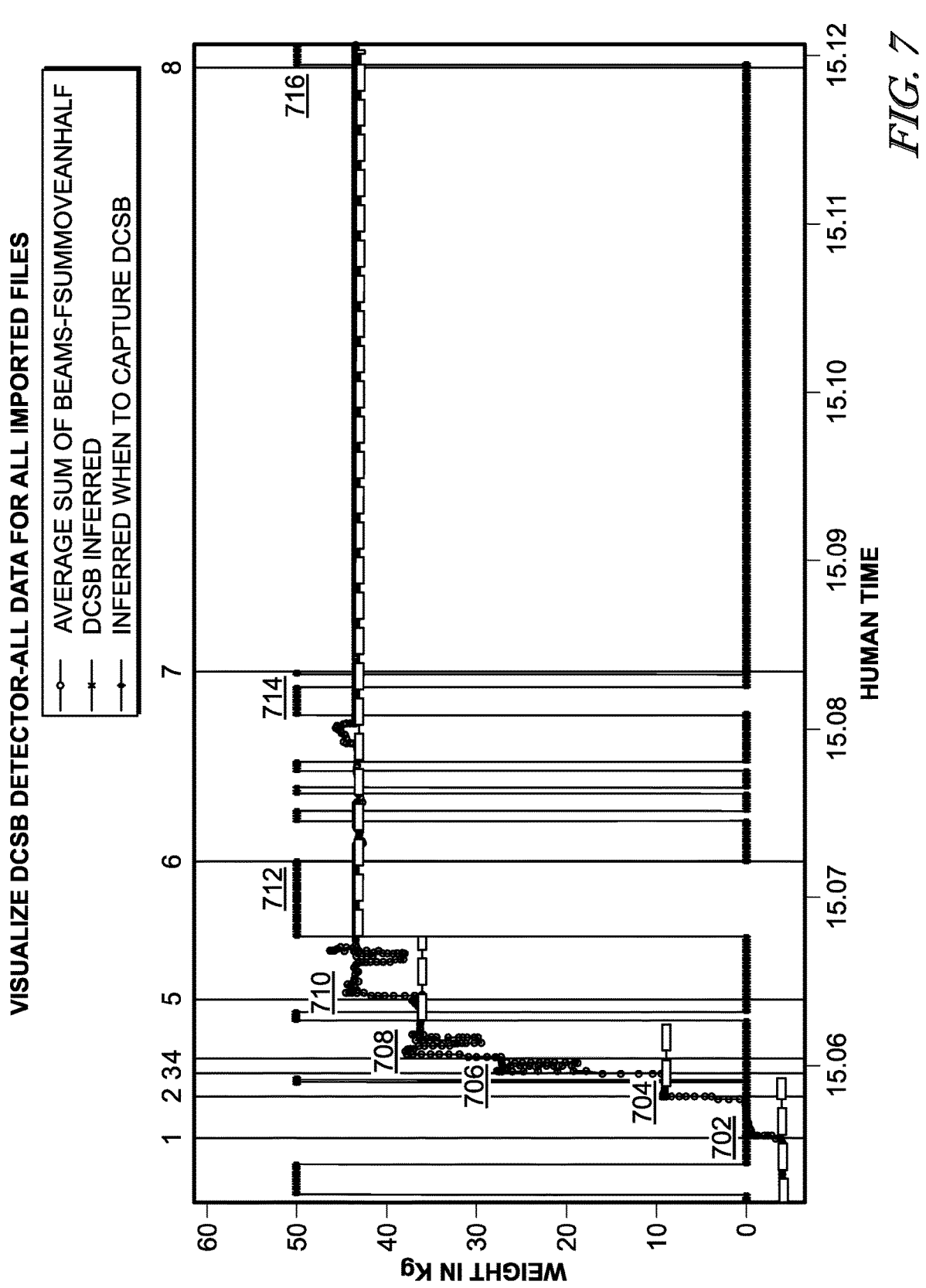
FIG. 7 is a schematic illustrating a DC sum of beams algorithm.

FIG. 7 shows the results of a spot test conducted to verify if the DCSB or patient weight is being updated appropriately, in the absence of any motion detection. The patient support apparatus such as the bed 10 is zeroed in step 702, and a 20 lb. weight is added in step 704. About 40 lbs. (consecutive 20 lb. weights) is added in step 706. Another 20 lb. weight is added in step 708. An oscillating test fixture of about 10 lbs. is added in step 710. The oscillating feature is turned on in step 712 and turned off in step 714.

The circles represent the average sum of load cells 66, 68, 70, and 72 over 10 seconds. The dashed lines represent the DCSB, inferring the weight on the bed 10. The solid line is a representation of when the algorithm will update the DCSB. In one embodiment, the algorithm will update the DCSB is the solid line is ~ 45 and will not update the DCSB when the solid line is ~ 0.

FIG. 7 shows that the DCSB is updated per the intended design. An increase in the solid lines indicates that DCSB will be updated. In steps 704-706, when weights are added in increments, and the new value of DCSB is updated (dashed lines) about 5 seconds after the weight settles and there is no any longer movement on the bed 10. An oscillating mass used to induce motion in steps 710-716. During the period between steps 714 and 716, the solid line is always at zero as motion is detected and the DCSB is not updated. Transients are observed around the 15:08 time point when the oscillating fixture is turned on. At this time, the solid line is zero, and the DCSB does not update to that of the actual transient forces (circles).

Once motion is identified at step 98, the motion is discriminated at step 80 between NPMA and patient motion of either LPM or SO. If NPMA is identified at step 80, then the signal data is disregarded. However, confirmation and characterization of LPM or SO at step 80 is further analyzed at step 102 to establish a degree of motion. At step 102, in the illustrative embodiment, the motion can be distinguished between an egress, a large self-offloading patient movement (SO), a major lateral patient motion (LPM) and/or a small self-offloading patient movement (SO), or a slight lateral patient motion. Once the inference as to the type of patient motion is complete at step 102, the information is then moved to a database associated with the patient as step 104. For example, at step 104 the patient's medical record can be updated, based on the inference identify, objectively, the patient's motion and behavior such as regular self-offloading patient movement (SO), major lateral patient motions (LPMs), slight LPMs, or ingress or egress with or without caregiver assistance.

While the algorithm 78 of FIG. 6 has been established as a successful approach to drawing inferences regarding the characterization of patient motion, considering the entire structure of the bed 10, additional information is available that may be fused with the load cell signal data to provide and even more accurate indication of the status of the patient and assist in improving the inferences drawn. Specifically, the patient is supported on the mattress 18 and portions of the patient are supported on the inflated zones 36, 38, 40, and 42. The respective head zone sensor 82, a seat zone sensor 84, a thigh zone senor 86, and a foot zone sensor 88 are each gathering data in real time and the air module 52 is in communication with the scale module 50 and controller 28 so that data can be shared to further inform the analysis.

Still further, it should be understood the closed-system conservation of energy principles discussed above with regard to the load cells 66, 68, 70, and 72 hold with regard to the collective air pressure sensors 82, 84, 86, 88 and the load cells 66, 68, 70, 72 all-together. In other words, changes in energy at one inflatable zone 36, 38, 40, or 42 should be conserved, but may not be conserved as measure only by the air pressure sensors 82, 84, 86, 88, but some of the energy may be transferred away from the sensors 82, 84, 86, 88 and measured at one or more of the load cells 66, 68, 70, 72. Similarly, energy transferred away from one of the load cells 66, 68, 70, 72 and be effectively measured by one or more of the air pressure sensors 82, 84, 86, 88. This is best understood with an appreciation for the relative flexibility of the inflatable zones 36, 38, 40, or 42 and mattress 18 in total. The ability of the mattress 18 to absorb "shocks" without transferring the concomitant energy change to the load cells 66, 68, 70, 72 by transferring the energy to stretching fabric or compressing air within the zones 36, 38, 40, 42 confounds the analysis.

However, following the basic principles of conservation of energy, for movements considered to be NPMAs, a simple test to monitor for net changes in energy in the entire system of sensors will provide a high confidence level that the detected movement is, or is not, a true patient movement. In effect, the net kinetic energy being measured by the air pressure sensors 82, 84, 86, 88 and load cells 66, 68, 70, 72 should stay relatively constant, other than the theoretical variations due to heat transfer. Finally, the implementation requires the controller 28 to account for energy added to the system by the operation of components of the bed 10 such as the blower 106 or various drive motors that move components of the frame 34, such as the head section 44. The implementation also requires that any system based noise is accounted for and not added to the energy balance. In some embodiments, removal of noise may entail using one or more force transducers 902 or using algorithms such as adaptive filtering.

The control system 26 further includes a communications interface 108 that is operable, under the control of the controller 28, to communicate with the hospital information system 32 through a communications infrastructure 110 to share the patient health characterization, whether that be a mobility score, an activity score, a consciousness score, or any other objective score based on the output from the bed 10 acting as a sensor to objectively measure the motions made by the patient and characterizing the type of motions patient is making.

In one embodiment, adaptive filtering is implemented to account for any spurious noise in the system. The noise is characterized when the signal of interest is not present. In some embodiments, the signal is the always coming from the patient. When the patient is not present on the patient support apparatus such as the bed 10, the signal is captured and captured, the noise is characterized and translated into filter parameters. The filter parameters are then and reapplied in real time.

Figure 8D:
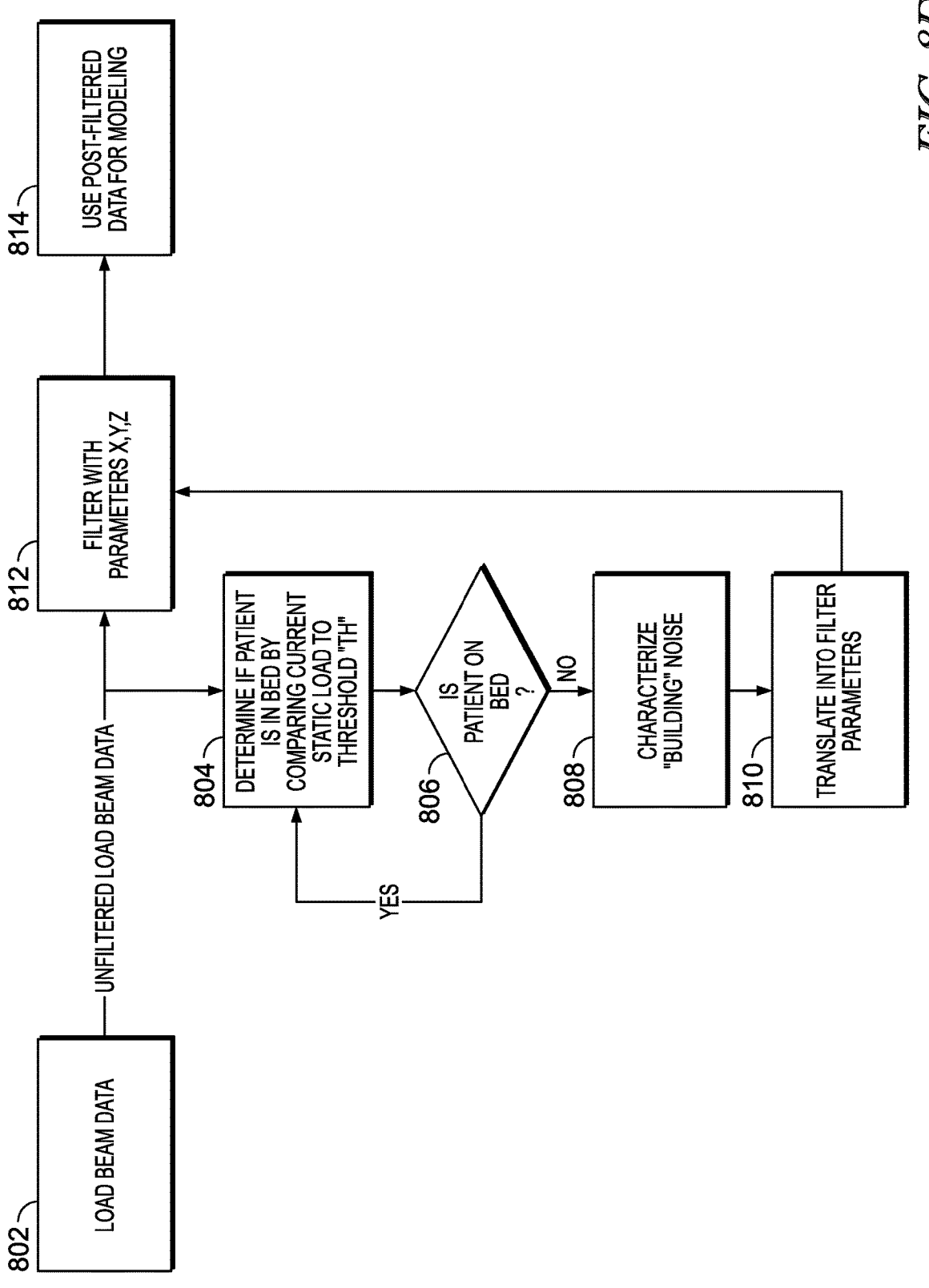
FIG. 8D is a flowchart illustrating adaptive filtering to account for building noise.

FIG. 8D illustrates a system that uses simple thresholds (TH) to determine when a patient is in or out of the patient support apparatus such as the bed 10. In step 802, unfiltered load cell 66, 68, 70, 72 data is determined by the system. In steps 804, the current static load is compared to a threshold (TH). In step 806, the comparison is used to determine if the patient is in or out of the bed 10. If the patient is out of the bed 10, building noise is characterized in step 808. If the patient is in the bed 10, step 804 is repeated. The captured noise is translated into filter parameters in step 810. The unfiltered load cell 66, 68, 70, 72 data is filtered with the filter parameters in step 812. The post filtered data is used for modeling step 814.

In one embodiment, as shown in FIG. 9, the noise in the system may be filtered by using one or more force transducers 902 in the patient support apparatus such as the bed 10. The force transducer may be a secondary or reference load cell 902 attached to an intermediate frame 904 that is not supporting the weigh frame 30 or the sleep deck such as upper frame 34. The secondary load cell 902 may not affected by the patient movements or weight.

Some small mass 908 may be attached to the reference load cell 902, but the reference load cell 902 may not be rigidly mounted to the weigh frame 30 or sleep deck such as upper frame 34. Building noise 906 may still propagate up through the base frame 22 and weigh frame 30 to the mass 908, as the noise 906 propagates through what is sensed on the weigh frame 30. Another embodiment might use a different kind of sensor, such as an accelerometer that is attached to the weigh frame 30. The accelerometer may also sense building noise 906.

With any type of force transducer or secondary load cell 902, two further embodiments may be used to compensate for building noise. In one embodiment, noise from one sensor is directly subtracted from the other sensor. This is a hardware or software topography called a "differential signal" and used to compensate for noise, drift in the sensor, or to improve robustness against other factors that are not what is being sensed. In another embodiment, the noise profile is characterized via an A/D or DSP to determine the amount of noise present and at the level of noise present. The characterized noise profile is then used to change filtering parameters.

Although this disclosure refers to specific embodiments, it will be understood by those skilled in the art that various changes in form and detail may be made without departing from the subject matter set forth in the accompanying claims.

The invention claimed is:

1. A patient support apparatus located on a floor comprising:

a plurality of load cells, a frame supported on the load cells, a mattress including a plurality of inflatable zones positioned on the frame, the mattress and frame cooperating to direct any patient load through the mattress and frame to the load cells, a vibration sensor not supported on the load cells, the vibration sensor operable to create a noise profile to compensate for noise from the floor on which the patient support apparatus is located, and a control system including a controller, the controller receiving a separate signal from each of the plurality of load cells and the vibration sensor, monitoring energy detected by each of the load cells, and processing the signals to predict, based on transient changes in the signals, when there is no motion detected, to capture an offset with no motion content, and automatically updating a patient profile in a patient record.

2. The patient support apparatus of claim 1, wherein the controller is operable to predict a minimum number of instances of no motion when there is motion.

3. The patient support apparatus of claim 2, wherein the controller uses a decision threshold to determine the probability of the motion, wherein if the probability of motion is under 0.05, the controller infers that there is no motion.

4. The patient support apparatus of claim 3, wherein the controller is further operable to determine no motion, if there is no motion detected for a pre-determined time period.

5. The patient support apparatus of claim 4, wherein the controller is further operable to determine a total energy acting on the load cells as an average of total energy acting on the loads cells for about half the pre-determined time period.

6. The patient support apparatus of claim 4, wherein the pre-determined time period is about 5 continuous seconds.

7. The patient support apparatus of claim 1, wherein the controller is able to detect any difference in patient weight in real time.

8. The patient support apparatus of claim 7, wherein any difference in the patient weight detected in real time by the controller is transmitted to one or more applications in one or more systems being used by the patient or the patient's caregiver.

9. The patient support apparatus of claim 1, wherein the detection of no motion accounts for noise in the patient support apparatus.

10. The patient support apparatus of claim 9, wherein the controller further comprises adaptive filtering to mitigate the noise in the patient support apparatus.

11. The patient support apparatus of claim 1, wherein the vibration sensor comprises one of, a secondary load cell, a force transducer, or an accelerometer.

12. A system comprising:

a patient support surface including a plurality of inflatable zones, a plurality of load cells supporting the patient support surface, a vibration sensor not supported on the load cells, the vibration sensor operable to create a noise profile to compensate for noise from a floor on which the patient support surface is located, and a controller receiving a separate signal from each of the plurality of load cells and the vibration sensor, the processing the signals to predict, based on transient changes in the signals, when there is no patient motion, and automatically updating a patient record to reflect the characterization of the patient motion.

13. The system of claim 12, wherein the controller further comprises adaptive filtering to mitigate the noise in the system.

14. The system of claim 13, wherein adaptive filtering comprises capturing and characterizing the noise when the patient in not supported on the patient support surface, translating the noise into filter parameters, designing a filter, applying and updating the filter parameters to the filter in real time.

15. The system of claim 13, wherein a source of the noise is the floor on which the system is located and transmitted to the vibration sensor, the mattress, and the frame through a base of the patient support apparatus.

16. The system of claim 15, wherein the noise profile is translated into filter parameters for adaptive filtering of the noise in real time.

17. The system of claim 16, the filter parameters are used in an adaptive filter to compensate for the noise from the floor on which the system is located.

18. The method of claim 17, wherein the controller is configured to detect any difference in patient weight in real time.

19. The method of claim 18, wherein any difference in the patient weight detected in real time by the controller is transmitted to one or more applications in one or more systems being used by the patient or the patient's caregiver.

20. The method of claim 17, wherein the detection of no motion accounts for noise in the patient support apparatus.

21. The method of claim 20, further comprising implementing adaptive filtering to mitigate the noise in the patient support apparatus.

22. The method of claim 21, wherein the vibration sensor comprises one of, a secondary load cell, a force transducer, or an accelerometer.

23. A method of updating weight of a person on a patient support apparatus comprising an inflatable mattress having multiple inflatable zones, the method comprising the steps of:

monitoring signals from a plurality of load cells, the plurality of load cells supporting the inflatable mattress;

monitoring signals from a vibration sensor not supported on the load cells;

monitoring the energy detected by each of the load cells and the vibration sensor;

processing the signals from the load cells and the vibration sensor to identify any motion;

upon detection of no motion, capturing an offset with no motion content, and automatically updating a record associated with the particular person to reflect the person's weight.

24. The method of claim 23, wherein processing the signals from the load cells to identify any motion comprises a controller that is operable to predict a minimum number of instances of no motion when there is motion.

25. The method of claim 24, wherein the method further comprises the controller using a decision threshold to determine the probability of motion, wherein if the probability of motion is under 0.05, the controller infers that there is no motion.

26. The method of claim 25, wherein the controller is further operable to determine no motion, if there is no motion detected for a pre-determined time period.

27. The method of claim 26, wherein the controller is further operable to determine a total energy acting on the load cells as an average of total energy acting on the loads cells for about half the pre-determined time period.

28. The method of claim 26, wherein the pre-determined time period is about 5 continuous seconds.

* * * * *